(12) United States Patent
Plaβky et al.

(10) Patent No.: US 8,709,017 B2
(45) Date of Patent: Apr. 29, 2014

(54) MOUNTING FOR A BONE DRILL AND BONE DRILL MOUNTING SYSTEM

(75) Inventors: Norman Plaβky, Erfurt (DE); Timo Neubauer, Poing (DE); Julia Fessler, Feldkirchen (DE)

(73) Assignee: Brainlab AG, Feldkirchen (DE)

( * ) Notice: Subject to any disclaimer, the term of this patent is extended or adjusted under 35 U.S.C. 154(b) by 1275 days.

(21) Appl. No.: 11/950,441

(22) Filed: Dec. 5, 2007

(65) Prior Publication Data

US 2009/0005785 A1  Jan. 1, 2009

Related U.S. Application Data

(60) Provisional application No. 60/882,736, filed on Dec. 29, 2006.

(30) Foreign Application Priority Data

Dec. 5, 2006  (EP) ..................... 06025111

(51) Int. Cl.
| | | |
|---|---|---|
| *A61B 17/58* | (2006.01) | |
| *A61B 17/60* | (2006.01) | |
| *A61F 2/00* | (2006.01) | |
| *A45D 42/14* | (2006.01) | |
| *F16B 47/00* | (2006.01) | |

(52) U.S. Cl.
USPC .......... 606/96; 606/89; 248/205.5; 248/206.2

(58) Field of Classification Search
USPC ............ 606/89, 96; 600/426, 431; 248/205.5, 248/206.2
See application file for complete search history.

(56) References Cited

U.S. PATENT DOCUMENTS

| | | | | |
|---|---|---|---|---|
| 989,839 | A * | 4/1911 | Powler | 604/276 |
| 1,128,459 | A * | 2/1915 | Kleine | 601/112 |
| 1,994,516 | A * | 3/1935 | Hawn | 408/56 |
| 2,146,859 | A | 2/1939 | Seklehner | |
| 2,417,539 | A * | 3/1947 | Aronson | 408/72 R |
| 2,657,893 | A | 11/1953 | Puckert | |
| 2,910,895 | A * | 11/1959 | Winslow | 408/10 |
| 3,030,017 | A | 2/1962 | Watson | |
| 3,207,150 | A * | 9/1965 | Uddenberg | 600/431 |
| 3,654,047 | A | 4/1972 | Berkowitz | |
| 3,728,891 | A * | 4/1973 | Hall, Jr. | 72/465.1 |
| 3,926,192 | A * | 12/1975 | Van Maren | 606/119 |
| 3,955,563 | A | 5/1976 | Maione | |
| RE30,317 | E * | 7/1980 | Lubbers et al. | 600/363 |
| 4,291,866 | A | 9/1981 | Petersen | |
| 4,369,793 | A | 1/1983 | Staver et al. | |
| 4,814,185 | A | 3/1989 | Jones | |
| 5,259,836 | A * | 11/1993 | Thurmond et al. | 600/431 |
| 5,312,408 | A | 5/1994 | Brown | |
| 5,345,935 | A * | 9/1994 | Hirsch et al. | 600/376 |

(Continued)

FOREIGN PATENT DOCUMENTS

| | | |
|---|---|---|
| EP | 0 797 958 A1 | 10/1997 |
| EP | 0 923 906 | 6/1999 |

(Continued)

*Primary Examiner* — David Bates
(74) *Attorney, Agent, or Firm* — Tucker Ellis LLP

(57) ABSTRACT

A mounting device for arranging a medical apparatus on a bone includes a fastening portion for fixing the mounting device to the bone. The fastening portion is configured to interface with the bone and operative to fix the mounting device to the bone using a vacuum.

11 Claims, 4 Drawing Sheets

(56) References Cited

U.S. PATENT DOCUMENTS

| | | | |
|---|---|---|---|
| 5,497,771 A * | 3/1996 | Rosenheimer | 600/323 |
| 5,507,741 A * | 4/1996 | L'Esperance, Jr. | 606/5 |
| 5,662,677 A | 9/1997 | Wimmer | |
| 5,752,962 A | 5/1998 | D'Urso | |
| 5,897,882 A | 4/1999 | Gonzalez et al. | |
| 6,156,069 A | 12/2000 | Amstutz | |
| 6,338,619 B1 | 1/2002 | Rusch | |
| 6,345,192 B1 | 2/2002 | Feucht et al. | |
| 6,425,565 B1 * | 7/2002 | Montague | 248/363 |
| 6,478,271 B1 | 11/2002 | Mulholland | |
| 6,595,999 B2 | 7/2003 | Marchione et al. | |
| 6,773,418 B1 * | 8/2004 | Sharrow et al. | 604/176 |
| 6,827,344 B1 * | 12/2004 | Ristau | 269/21 |
| 7,179,224 B2 | 2/2007 | Willis | |
| 7,195,429 B2 * | 3/2007 | Dods et al. | 408/67 |
| 7,338,020 B2 | 3/2008 | Magid | |
| 7,458,977 B2 * | 12/2008 | McGinley et al. | 606/130 |
| 2001/0029956 A1 | 10/2001 | Argenta et al. | |
| 2002/0049369 A1 | 4/2002 | Spence et al. | |
| 2004/0076484 A1 * | 4/2004 | Alam et al. | 408/79 |
| 2004/0082960 A1 | 4/2004 | Davison | |
| 2004/0127908 A1 | 7/2004 | Roman et al. | |
| 2004/0176659 A1 | 9/2004 | Peng et al. | |
| 2005/0033322 A1 | 2/2005 | Lau et al. | |
| 2005/0075632 A1 * | 4/2005 | Russell et al. | 606/53 |
| 2005/0119639 A1 | 6/2005 | McCombs et al. | |
| 2006/0245835 A1 * | 11/2006 | Hechtle et al. | 408/115 B |
| 2007/0123774 A1 * | 5/2007 | Gotte et al. | 600/426 |
| 2007/0218101 A1 * | 9/2007 | Johnson et al. | 424/423 |

FOREIGN PATENT DOCUMENTS

| | | |
|---|---|---|
| EP | 1 371 340 A1 | 12/2003 |
| WO | 93/06873 A1 | 4/1993 |
| WO | 03/096870 | 11/2003 |

* cited by examiner

MOUNTING FOR A BONE DRILL AND BONE DRILL MOUNTING SYSTEM

RELATED APPLICATION DATA

This application claims priority of U.S. Provisional Application No. 60/882,736 filed on Dec. 29, 2006, which is incorporated herein by reference in its entirety.

FIELD OF THE INVENTION

The invention relates generally to a mount for a bone drill and, more particularly, to a mount for a bone drill that is to be attached to the head of a femoral bone (Joint head).

BACKGROUND OF THE INVENTION

In order to attach a femoral component of a leg bone during re-surfacing in hip surgery, the femoral bone is prepared such that it obtains a specific shape. While preparing the femoral bone, it is desirable to avoid any kind of notching or weakening of the joint neck, since such weakening or notching can cause cracks or fractures.

A femoral implant component has a symmetrical inner shape with a central pin, and it is desirable to accurately define and realize the position and orientation of the hole for this central pin. During the re-surfacing treatment, a pilot drill hole is made for the central pin of the implant, and it is similarly desirable to place the pilot drill hole as accurately as possible, since all the subsequent working steps are based on this location.

In order to support this drilling process, various tools have been used to define the entry point and the axis for the drill hole. U.S. Pat. No. 6,156,069 discloses a gripping device which grips the femoral neck and can guide the drill. U.S. Pat. No. 6,595,999 B2 discloses a drill mounting attached as a frame, in which a probe is provided in order to ensure positioning. Directing fastening to the femoral head or to a plane face of the femoral head, following a milling procedure, is also known from U.S. Pat. No. 6,595,999 B2.

SUMMARY OF THE INVENTION

A bone drill mounting device in accordance with one aspect of the invention has a fastening portion for fastening to the bone. The fastening portion operates using vacuum suction. Thus, the fastening portion is fixed to the bone without having to encroach or otherwise damage the bone. This has various advantages.

First, the mounting device allows a drill to be fixedly orientated, and the surgeon is able to make a drill hole in a defined direction. Since the mounting device fixes the drill to the bone, the risk of the drill slipping off the surface of the bone is significantly reduced.

Also, no additional elements (pins, screws, grips, etc.) are necessary for attaching the mounting device to the bone. The stable connection to the bone is established by a difference in pressure; the drilling angle is similarly fixed in this way. Omitting screws or pins enables corresponding bone notches or bone damage (which can form the starting point for fractures or cracks) to be avoided. Further, avoiding the use of expendable products for fastening (e.g., bone screws or the like) lowers cost. Time is also saved, since establishing the vacuum merely involves suctioning off air, which in a suitable embodiment should transpire very quickly. Also, it is not necessary to additionally prepare the bone (for example by milling). The mounting device is simple and non-invasive to hand grip, and can very easily be combined with a navigation support, such that additional probes for verifying the orientation can likewise be omitted.

The fastening portion of the mounting device can include a fastening vacuum space or fastening vacuum area, and a valve means via which the pressure in the fastening vacuum space or fastening vacuum area can be regulated. The fastening vacuum space can be sealed by a sealing means that grips and/or forms a seal with the bone, in particular by a sealing skirt array around the fastening vacuum space or fastening vacuum area.

It is possible to arrange a drill guiding portion on the fastening portion, wherein the drill guiding portion can be moved relative to the fastening portion. The drill guiding portion can form an attachment that is sealed and can be shifted on the fastening portion, and which comprises a drill guide. The mounting device also can include a guiding vacuum space or guiding vacuum area that fixes the position of the drill guiding portion relative to the fastening portion when a vacuum is formed.

The vacuum can be used in various ways. It is possible to connect the fastening and guiding vacuum spaces or vacuum areas to each other, such that they form a single vacuum area or vacuum space. In this case, establishing the vacuum would serve both to fasten the mounting device to the bone and to orientate and fix the drill guide.

In another case, the vacuum spaces or vacuum areas for fastening and fixing could be separated from each other, such that the orientation of the drill can be performed independent of fastening the mounting device by applying separate vacuums. It is also in principle conceivable for only the drill guiding portion to be orientated and/or fixed using a vacuum.

A separate valve means can be provided for the drill guiding portion, via which the pressure in the guiding vacuum space or guiding vacuum area can be regulated.

A number of combinations of the bone drill mounting device with other medical apparatus or devices are envisioned. In particular, a bone drill mounting system can include a bone drill mounting device, such as has been described above in different embodiments, and a hand grip using which the mounting device can be held by means of a drill guide. The hand grip can be connected to a vacuum source and to the vacuum suction of the fastening portion, and in a specific embodiment, control devices for controlling the vacuum can be assigned to the hand grip. It is also possible to use the hand grip to control not only the suction of the fastening portion but also the fixing of the drill guiding portion by a vacuum, or one or both of these controls can be performed independently of each other.

Another bone drill mounting system, including a bone drill mounting device as descried herein, also can include one or more of the following elements:

- a medical navigation reference arranged in a determined position relative to a drill guide which is assigned to the mounting device;
- a medical navigation system that can ascertain the spatial position of the navigation reference;
- a vacuum source connected to the vacuum suction of the fastening portion; and/or
- control devices for controlling the vacuum in accordance with the spatial position of the navigation reference, and thus in accordance with the spatial position of the drill guide.

The latter embodiment cited above thus enables the bone drill mounting device to be simply and directly incorporated into a medical navigation.

BRIEF DESCRIPTION OF THE DRAWINGS

The forgoing and other features of the invention are hereinafter discussed with reference to the drawings.

DETAILED DESCRIPTION

Figure 1:
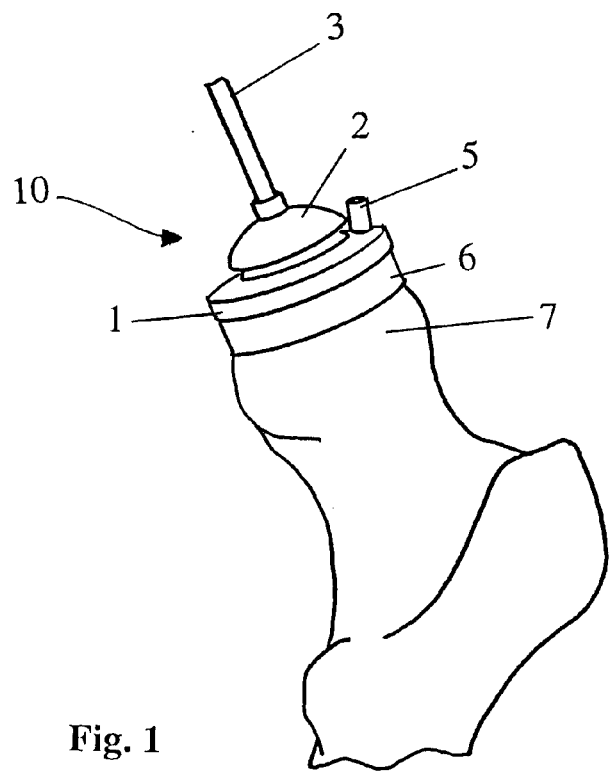
FIG. 1 is a perspective view of an exemplary bone drill mounting device in accordance with the invention, arranged on a bone.

Each of FIGS. 1 to 4 show an exemplary bone drill mounting device that as a whole bears the reference sign 10. The bone drill mounting device 10 includes a fastening portion 1 that is placed over the joint head 7 of a femoral bone, which has not been treated. The bone is in contact only with sealing skirts 6. A vacuum is formed in a circular space between the inner and outer skirt 6, and holds the fastening portion 1 on the joint head 7. The vacuum is indicated as a lower pressure in FIG. 2 by P1, while the higher outer pressure is indicated by P0. The higher outer pressure P0 presses the mounting 10 onto the joint head 7 until supporting pins 9, only one of which can be seen in each of FIGS. 2 to 4, come to rest on the bone.

Figure 2:
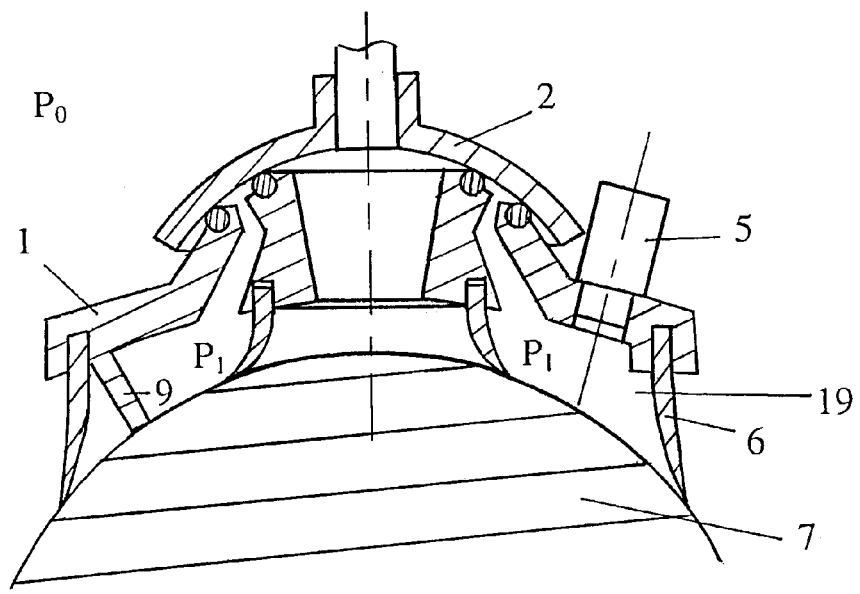
FIGS. 2 to 4 illustrate exemplary bone drill mounting devices in a sectional view and arranged on the bone (femoral joint head)
Figure 3:
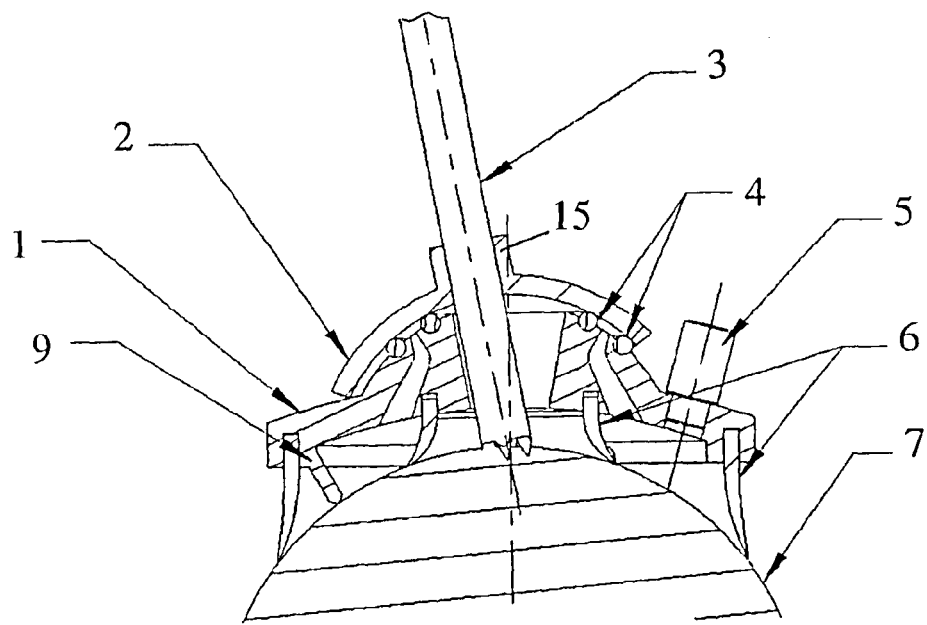

The guiding portion 2 of the mounting device 10 can be placed on sealing rings 4 (FIGS. 3 and 4) on top of the fastening portion 1. The guiding portion 2 can be arranged such that it can be shifted, and two different positions are shown in FIGS. 2 and 3. Using this shifting arrangement, the drilling angle can be adjusted; by arranging the fastening portion 1, the entry point can be selected and defined.

The embodiment in FIGS. 1, 2 and 3 has a single valve 5, which can be used to suction air out of the vacuum space 19, and in this embodiment, the fastening portion 1 is positioned in order to select the entry point, the guiding portion 2 is shifted and/or rotated until the entry angle is correct, and the vacuum is then applied via the valve 5, which fixes both the fastening portion 1 and the guiding portion 2 such that drilling can be performed in a defined and correctly orientated manner.

Figure 4:
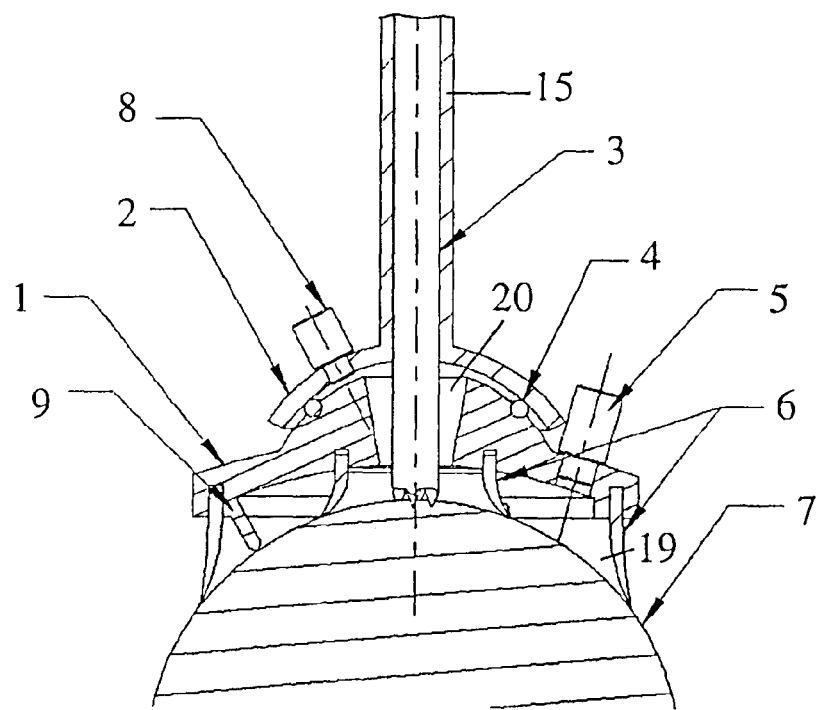

An embodiment which deviates slightly from this is shown in FIG. 4, wherein two vacuum systems are provided which are separate and operate independently of each other. One vacuum system charges the vacuum space 19 via the valve 5 to fasten the fastening portion 1, and the second vacuum system charges the vacuum space 20 with a vacuum via the valve 8 to fix the guiding portion 2. Fastening can therefore be performed independently of orientation of the drill 3.

Figure 5:
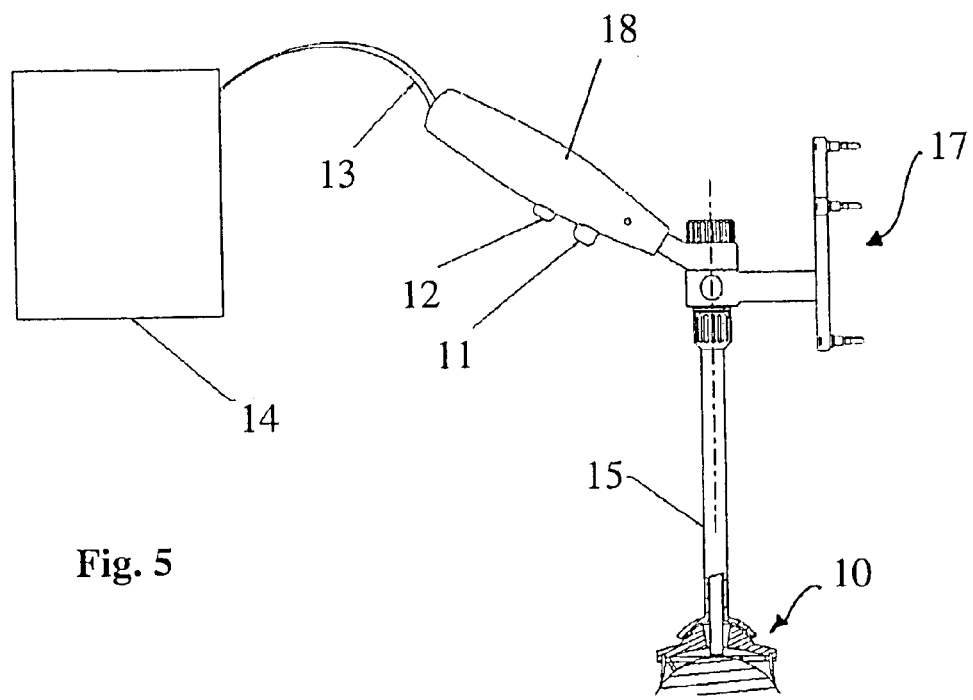
FIGS. 5 and 6 illustrate an exemplary bone drill mounting system in accordance with the invention, comprising a hand grip and vacuum source.
Figure 6:
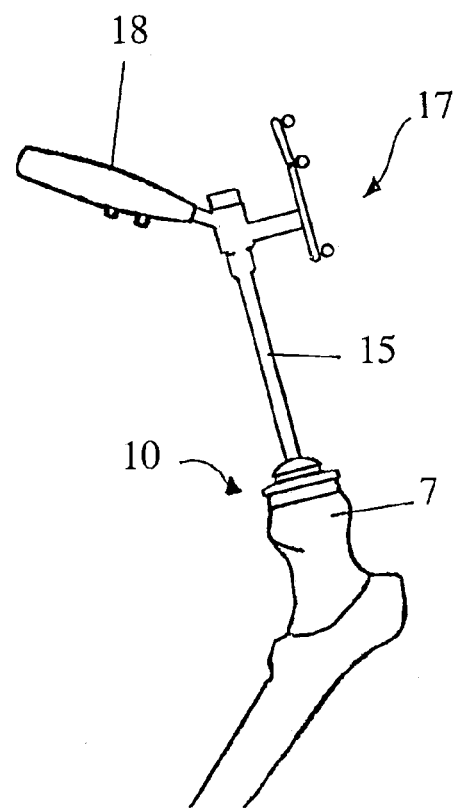

FIGS. 5 and 6 show another exemplary bone drill mounting system. The mounting system of FIGS. 5 and 6 include a vacuum source 14, wherein FIG. 6 provides a perspective view. The vacuum is generated directly and centrally in the corresponding spaces of the mounting via the drill guide 15. The drill guide 15 is connected to a navigation reference 17, which is discussed further below. The hand grip 18 comprising the two push buttons 11 and 12 is also attached to the drill guide, wherein the hand grip comprises a lead 13 to the vacuum source 14.

In this embodiment, a vacuum is for example generated or released again in the bone drill mounting 10 via the buttons 11 and 12. The drill guide 15 can be orientated using the grip, before being fixed by applying the vacuum.

Figure 7:
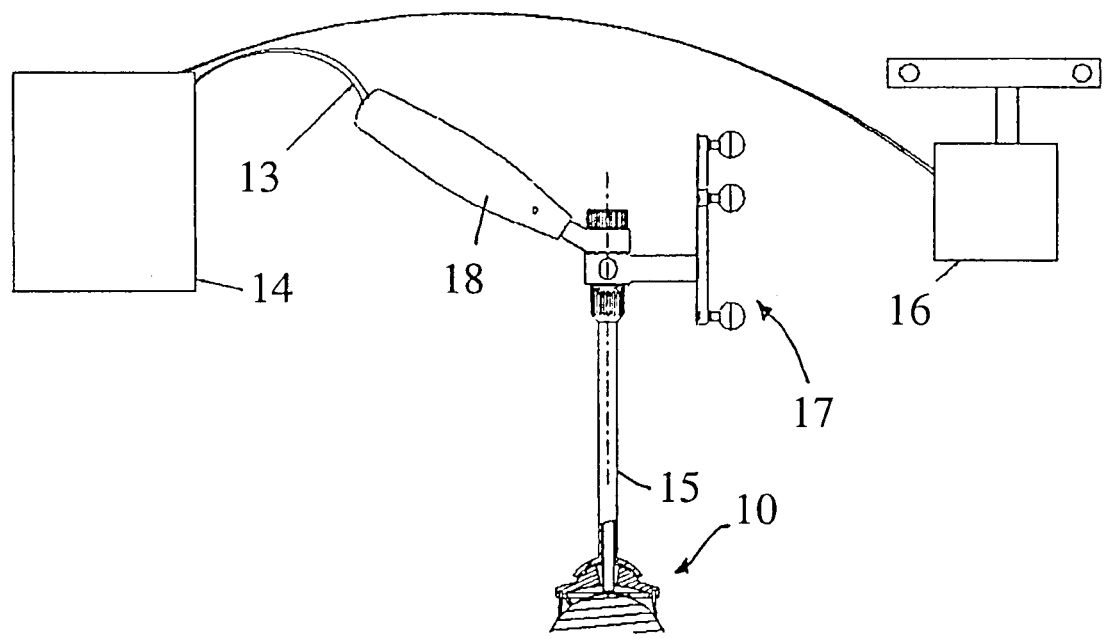
FIG. 7 illustrates the incorporation of an exemplary mounting system in accordance with the invention into a medical navigation system.

The mounting system can be incorporated into a medical navigation system by means of the navigation reference 17 already mentioned above, as shown in FIG. 7, which shows how the navigation system 16 comprising tracking cameras (not indicated) is arranged such that it can determine the position and orientation of the navigation reference 17. Once the correct position for the drilling guide 15 has then been found by means of the grip 18, an automatic sequence can be performed, since, as shown, the navigation system 16 is connected to the vacuum source 14. Thus, once the orientation of the drill guide 15 is correct, this can be confirmed by the navigation system 16 via the navigation reference 17, and this confirmation can automatically trigger the suctioning of air from the mounting 10 via the drill guide 15, the grip 18 and the lead 13 and with the aid of the vacuum source 14. This ensures that the drill hole is made in precisely the orientation and position necessary to allow an implant to be optimally placed at a later time.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A mounting device for arranging a medical apparatus on a bone, comprising a fastening portion for fixing the mounting device to the bone, said fastening portion having a body and an inner skirt and an outer skirt depending from the body for interfacing with the bone and operative to fix the mounting device to the bone using a vacuum, the inner and outer skirts forming therebetween an annular vacuum space that when evacuated holds the fastening portion to the bone, a first valve operative to regulate a pressure in the annular vacuum space and a guiding portion for guiding the medical apparatus, said guiding portion arranged on the body for movement relative to the body to allow the medical apparatus to be angled relative to the bone, wherein the guiding portion is movable relative to the fastening portion between a plurality of positions and the guiding portion comprises a guiding vacuum space that fixes the guiding portion relative to the fastening portion at each of the plurality of positions when a vacuum is formed in the guiding vacuum space, and a second valve operative to regulate a pressure in the guiding vacuum space, the second valve enabling a vacuum to be drawn within the guiding vacuum space via the second valve.

2. The mounting device according to claim 1, wherein the guiding portion comprises a drill guide.

3. The mounting device according to claim 1, wherein the guiding portion forms an attachment that can be rotatably shifted on the fastening portion.

4. The mounting device according to claim 3, wherein the guiding portion includes a drill guide.

5. The mounting device according to claim 1, wherein the guiding portion includes a sealing member that seals the guiding vacuum space with a surface of the fastening portion.

6. The mounting device according to claim 1, wherein the vacuum space and the annular vacuum space for fastening and guiding are separate and independent from each other.

7. The mounting device according to claim 1, wherein the inner and outer skirts have respective flexible portions for conforming to a surface of the bone.

8. A mounting system for arranging a medical apparatus on a bone, comprising:
   a mounting device including a fastening portion for fixing the mounting device to the bone, said fastening portion having a body and an inner and outer skirt depending from the body for interfacing with the bone and operative to fix the mounting device to the bone using a vacuum, the inner and outer skirts forming therebetween an annular vacuum space that when evacuated holds the fastening portion to the bone;
   a first valve operative to regulate a pressure in the annular vacuum space;
   a guiding portion for guiding the medical apparatus, said guiding portion arranged on the body for movement relative to the body to allow the medical apparatus to be angled relative to the bone, wherein the guiding portion is movable relative to the fastening portion between a plurality of positions and the guiding portion comprises a guiding vacuum space that fixes the guiding portion relative to the fastening portion at each of the plurality of positions when a vacuum is formed in the guiding vacuum space, and a second valve operative to regulate a pressure in the guiding vacuum space, the second valve enabling a vacuum to be drawn within the guiding vacuum space via the second valve; and
   a hand grip attached to the guiding portion.

9. The mounting system according to claim 8, said hand grip operatively coupled to a vacuum source and to the annular vacuum space of the fastening portion, said hand grip further including control devices for controlling the vacuum applied to the annular vacuum space.

10. The mounting device according to claim 8, wherein the inner and outer skirts have respective flexible portions for conforming to a surface of the bone.

11. A mounting system for arranging a medical apparatus on a bone, comprising:
    a mounting device including a fastening portion for fixing the mounting device to the bone, said fastening portion configured to interface with the bone and operative to fix the mounting device to the bone using a vacuum, the fastening portion including an inner skirt and an outer skirt forming therebetween an annular vacuum space that when evacuated holds the fastening portion to the bone, and a guiding device;
    a medical navigation reference arranged in a determined position relative to the guiding device;
    a medical navigation system operative to ascertain a spatial position of the navigation reference;
    a vacuum source operatively coupled to the fastening portion via a first valve operative to regulate a pressure in the annular vacuum space;
    control devices for controlling the vacuum based on the spatial position of the navigation reference and/or the spatial position of the guiding device; and
    a guiding portion for guiding the medical apparatus, said guiding portion arranged on the body for movement relative to the body to allow the medical apparatus to be angled relative to the bone, wherein the guiding portion is movable relative to the fastening portion between a plurality of positions and the guiding portion comprises a guiding vacuum space that fixes the guiding portion relative to the fastening portion at each of the plurality of positions when a vacuum is formed in the guiding vacuum space; and a second valve operative to regulate a pressure in the guiding vacuum space, the second valve enabling a vacuum to be drawn within the guiding vacuum space via the second valve.

* * * * *